(12) United States Patent
Noble

(10) Patent No.: US 7,548,773 B2
(45) Date of Patent: Jun. 16, 2009

(54) DEVICES AND METHODS FOR MEASURING CLINICALLY RELEVANT ANALYTES IN FLUIDS

(75) Inventor: Michael Noble, London (GB)

(73) Assignee: PA Consulting Services Ltd., London, Greater London (GB)

( * ) Notice: Subject to any disclaimer, the term of this patent is extended or adjusted under 35 U.S.C. 154(b) by 212 days.

(21) Appl. No.: 10/589,532

(22) PCT Filed: Feb. 16, 2005

(86) PCT No.: PCT/GB2005/000550

§ 371 (c)(1),
(2), (4) Date: Nov. 6, 2006

(87) PCT Pub. No.: WO2005/080970

PCT Pub. Date: Jan. 9, 2005

(65) Prior Publication Data

US 2007/0202606 A1     Aug. 30, 2007

(30) Foreign Application Priority Data

Feb. 16, 2004    (GB) ................................. 0403369.2

(51) Int. Cl.
*A61B 5/05* (2006.01)
*A61B 5/157* (2006.01)

(52) U.S. Cl. ...................... 600/347; 600/345; 600/352

(58) Field of Classification Search ............ 250/339.09, 250/370.09; 435/7.91; 436/164; 600/322, 600/316, 345, 347, 352

See application file for complete search history.

(56) References Cited

U.S. PATENT DOCUMENTS

| 4,686,479 A | 8/1987 | Young et al. |
| 5,304,348 A | 4/1994 | Burd et al. |
| 5,512,491 A * | 4/1996 | Mehkeri et al. ............. 436/177 |
| 5,962,215 A | 10/1999 | Douglas et al. |

(Continued)

FOREIGN PATENT DOCUMENTS

WO    WO 99/05512    2/1999

(Continued)

OTHER PUBLICATIONS

International Search Report of PCT/GB2005/000550 mailed Jun. 16, 2005.

*Primary Examiner*—David P Porta
*Assistant Examiner*—Mark R Gaworecki
(74) *Attorney, Agent, or Firm*—Nixon & Vanderhye P.C.

(57) ABSTRACT

Methods and devices for the measurement of clinically relevant analytes in fluids are provided. The devices and methods are particularly relevant for detection of glucose in blood and allow internal calibration of measurements. One device includes a flow path for conducting the fluid through the device; a predetermined amount of the analyte arranged on the flow path such that the analyte mixes with fluid that passes it to form a calibration sample of the fluid and detector means arranged on the flow path for detecting respective analyte levels in an unadulterated sample of the fluid and in the calibration sample. Another device provides a predetermined amount of a calibration analyte of a different species to the clinically relevant analyte arranged on the flow path, and first and second detector means for detecting the levels of the clinically relevant analyte and the calibration analyte.

35 Claims, 1 Drawing Sheet

U.S. PATENT DOCUMENTS

Figure 1:
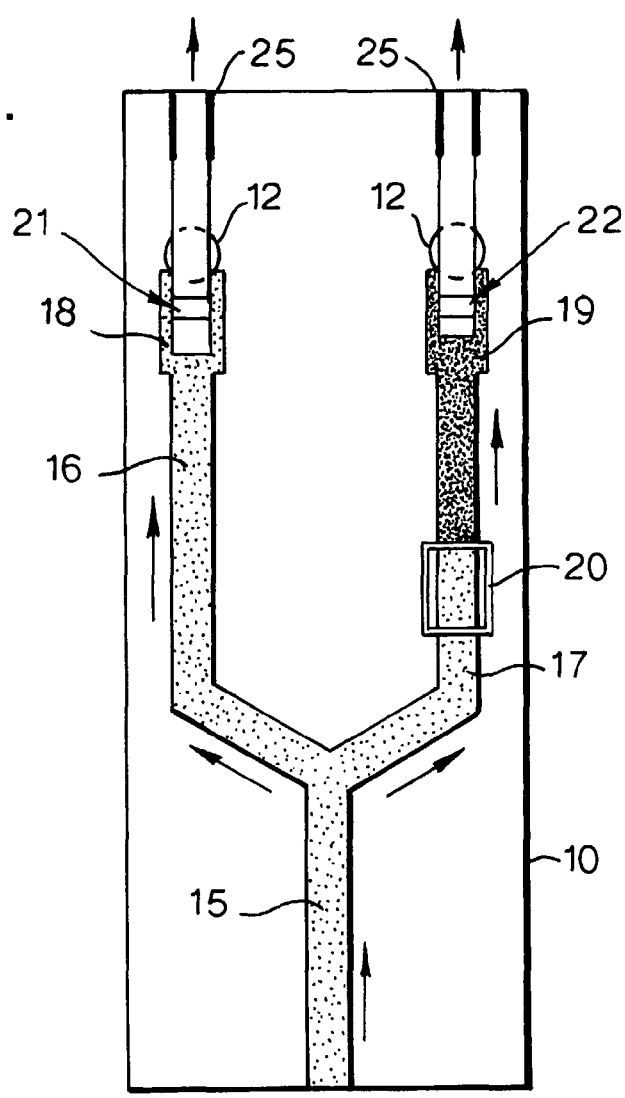

| | | |
|---|---|---|
| 6,287,451 B1 | 9/2001 | Winarta et al. |
| 6,551,842 B1 | 4/2003 | Carpenter |
| 6,558,916 B2 * | 5/2003 | Veerapandian et al. ........ 435/29 |
| 2003/0124739 A1 | 7/2003 | Song et al. |
| 2003/0143746 A1 * | 7/2003 | Sage, Jr. ........................ 436/8 |

FOREIGN PATENT DOCUMENTS

| | | |
|---|---|---|
| WO | WO 03/025573 | 3/2003 |
| WO | WO 2005/098431 | 10/2005 |

\* cited by examiner

DEVICES AND METHODS FOR MEASURING CLINICALLY RELEVANT ANALYTES IN FLUIDS

This application is the U.S. national phase of International application PCT/GB2005/000550 filed 16 Feb. 2005, which designated the U.S. and claims priority of GB 0403369.2, filed 16 Feb. 2004, the entire contents of which are herby incorporated by reference.

The present invention relates to devices and methods for testing clinically relevant analytes in samples of biological origin. It is particularly, but not exclusively concerned with methods and devices with improved accuracy for testing blood glucose levels.

Examples of clinically relevant analytes are indicators of cardiovascular, liver and kidney function (e.g. cholesterol, haemoglobin, electrolytes, metabolites), infectious agents (e.g. viruses, bacteria), disease state indicators (e.g. C-reactive protein, antibodies, cellular signalling factors, hormones) and therapeutic indicators (e.g. antibiotics and drugs) and in particular glucose. Examples of samples of biological origin include cerebrospinal fluid, urine, semen, saliva and in particular whole and fractionated blood.

In recent years, the management of diabetes has been considerably improved by the availability and use of self-testing Blood Glucose Monitoring (BGM) systems. These systems allow diabetics to determine their own blood glucose levels and, depending on the result, effectively self-medicate, for example by adjusting their therapy or dosage regime, or by adjusting their diet, thus maintaining their glucose levels within a relatively narrow band on either side of what is considered to be a healthy level.

This ability for diabetics to test and consequently control their own blood glucose levels tends to result in a lower incidence of diabetes related complications, as evidenced by the 1993 Diabetes Control and Complications Trial (DCCT, New England Journal of Medicine 329 (14), Sep. 30, 1993).

Typical BGM systems include a sensor element which generates a signal in proportion to the level of glucose present in a test blood sample, and a transducer that converts the generated signal into a readable blood glucose level.

One common form of the sensor element is a strip containing a blood testing area and a series of electrodes attached to the strip which transmit the generated signal to a hand-held meter by means of electrical conductors such as wires.

The blood testing area includes a detector means which is specifically adapted to detect glucose in blood and to generate a signal in proportion to the concentration or total quantity of glucose present.

One example of such a glucose detector means is the so-called "enzyme electrode", where an enzyme such as glucose oxidase (GOD) converts glucose to gluconolactone with concomitant generation of hydrogen peroxide. The hydrogen peroxide generated during the oxidation of glucose is measured at an electrode surface, generating a current in proportion to the glucose concentration in the sample.

Other devices use a combination of different enzymes and/or redox couplers to enhance the sensitivity of the reaction, or use alternative electrochemical measurement techniques. The common factors to such devices are the use of a biological recognition agent (the enzyme) and a transduction device (the electrode arrangement).

Examples of the type of devices referred to above are supplied under the OneTouch brand from Lifescan (Milpitas, Calif.), the Accu-Chek brand from Roche Diagnostics (a division of Hoffman-La Roche Ltd, Basel, Switzerland) and the Glucometer brand from Bayer (Tarrytown, N.Y.).

However, the accuracy of the blood glucose readings generated by the BGM systems such as those described above can be adversely affected by a number of factors. For example:

1. Interfering substances may be present in the patient's blood. Some substances such as acetaminophen and ascorbate are electroactive and can themselves generate an electrical signal on being oxidised at an electrode surface.
2. The oxygen availability at the electrode surface may vary. Oxygen is required to drive the GOD-catalysed, hydrogen peroxide-generating reaction described above. However the oxygen tension in the blood can vary significantly, depending on, amongst other things, the patient's haematocrit (Hct) level.
3. There may be variations in the manufacturing process. Generally strips forming the sensor elements are manufactured in large batches, and a calibration is determined for each batch to enable conversion of the electrical signal into a blood glucose reading. Generally the calibration set for a particular batch reflects the average performance of the strips in terms of their electrical response to blood glucose over the range of clinically feasible values. However, for any one particular test, it is likely that the strip used will deviate from that average and so the "batch calibration" applied to the signal generated by that strip will not provide an accurate reading of the blood glucose concentration in the tested sample.
4. User error may result in an improper testing procedure being applied. Although modern BGM systems are designed to reduce the likelihood of such errors, in some cases BGM systems will be used outside their specified conditions, for example in relation to temperature or altitude. Equally users may inadvertently affect the accuracy of their blood glucose readings by improper preparation of the blood test site, for example by insufficient drying of wet hands, resulting in a diluted blood sample.

As a result of these error sources, and others, commercial BGM systems currently available typically quote system accuracy levels (also know as "total error") of ±10-20% compared to a reference laboratory method.

Some BGM system manufacturers supply a "control solution" with a known concentration of glucose that can be used to determine whether the system is performing to specification.

The accuracy of a BGM system is an important feature which consumers use in their choice of product due to the direct impact that any error may have on their condition. Thus improving the accuracy of such systems is likely to have a corresponding increase in their popularity.

The accuracy level of BGM systems is also being made increasingly visible to users/consumers following the adoption of standard ISO 15197:2003 which states that companies developing such systems must now submit clinical evaluation results showing the proportion of data that falls within 5%, 10%, 15% and 20% error bands.

Moreover, it is well known that users do not tend to use their control solutions on a regular basis (see for example the FDA CDRH Focus Groups Survey, 2001, available at www.fda.gov/diabetes) and so there is little control of the actual accuracy of the BGM systems used by patients on a regular basis.

Several approaches to improve the accuracy of BGM systems have been proposed which focus on the above recognised sources of error.

For example, errors arising from manufacturing imprecision have been addressed to some extent by improving the control of the manufacturing process and investing in expensive new manufacturing technologies such as advanced printing techniques.

Attempts to minimise the impact of variable environmental conditions such as temperature and altitude have focussed on developing sensing mechanisms that modify the raw signal according to complex algorithms.

With regard to the variations in other properties of the blood sample, new chemistries and sensing technologies are being researched that in the long term might lead to the development of systems that are less sensitive to interferences. Selective membranes which can specifically exclude certain interferents from the sensing electrode have also been investigated.

Systems have also been developed which reduce, but may not eliminate, the likelihood of user error, particularly by controlling the user intervention, for example by controlling blood addition by the use of capillary fill tracks on the sensor strips.

As a result of these approaches and developments, gradually increasing system performance has occurred over a number of years. However, development of each of the above approaches generally requires significant investment of both time and money. Moreover, each of the above approaches only tends to address a single major source of error.

Whilst the above discussion has focussed primarily on BGM systems, similar problems are experienced with devices and methods for measuring other clinically relevant analytes.

The present invention seeks to improve the accuracy of such systems in a simple and cost-effective manner, and to provide new and improved devices for such systems.

At its broadest the present invention provides a method and a device for measuring levels of clinically relevant analytes, such as glucose, in a fluid wherein the measurement is subject to internal calibration.

A first aspect of the present invention provides a method for testing, in a portable device, levels of clinically relevant analytes in a fluid including the steps of:

mixing a sample of the fluid with a known amount of said analyte to form a calibration sample;

measuring the analyte level in an unadulterated sample of the fluid;

measuring the analyte level in said calibration sample; and adjusting the analyte level measured in said unadulterated sample using the analyte level measured in said calibration sample.

Preferably the clinically relevant analyte is glucose.

Typically the fluid is blood.

Preferably the steps of measuring involve measuring a concentration of the analyte. This may also include mixing a known volume of fluid with the known amount of said analyte in said mixing step.

By providing internal calibration of every sample tested, at the point of use, potential variations in the test result arising from sample effects (such as the presence of interferences, haematocrit level differences, etc.), environmental factors and manufacturing imprecision can be accounted for and the test results adjusted accordingly. Therefore errors in the test results can be substantially reduced, or even effectively eliminated.

By extension, if the method of the present invention is used to its fullest extent, then the weighting given to the 'batch calibration' of sensor strips in the calculation of analyte levels (e.g. blood glucose concentrations) might be reduced as the 'internal calibration' weighting is increased. The batch calibration procedure is generally a lengthy and costly process.

Therefore use of internal calibration according to the present invention could allow the amount of batch testing carried out to be reduced.

In the methods of the present invention, analyte levels (such as blood glucose concentrations) may be derived from an electrical signal generated by the sensing chemistry by reference to a calibration curve which relates analyte concentration to signal magnitude. Such 'batch calibration' curves can be generated based on average performance for a batch of strips and do not therefore take into account any particular error related to the individual measurement being made. The method of the present aspect may allow adjustment of the calculated analyte concentration for the unadulterated sample by taking into account the calculated analyte concentration from the calibration sample. By such an internal calibration method, errors relating to the individual measurement being made can be minimised.

The internal calibration may be applied to the unprocessed measurement of the analyte level in the unadulterated sample and an analyte level reading then generated from the adjusted analyte level.

Alternatively, the internal calibration may be applied to an analyte level reading generated from the measured analyte level in the unadulterated sample, thereby correcting it.

In particular embodiments of the methods of the present invention, analyte level readings may be generated by applying a calibration curve to an unprocessed measured analyte level or to an adjusted analyte level.

The methods of the present invention preferably also includes the step of introducing said fluid to a flow path, wherein said fluid flows along the flow path whilst said steps of measuring and mixing are carried out.

One particular algorithm that may be used to calculate an adjusted analyte concentration is:

$$Gl_{adj} = (Gl_{un} \times Q)/(Gl_{cal} - Gl_{un})$$

where $Gl_{adj}$, $Gl_{un}$, and $Gl_{cal}$ are respectively the adjusted analyte concentration, the analyte concentration measured in the unadulterated sample of the fluid, and the analyte concentration measured in the calibration sample and Q is the known increase in concentration of analyte in the calibration sample resulting from the addition of a known amount of the analyte to a known volume of sample.

In a development of this aspect of the present invention, the method further includes the steps of mixing a sample of the fluid with a second known amount of the analyte to form a second calibration sample, and measuring the analyte level in said second calibration sample, wherein the step of adjusting uses the analyte levels measured in both calibration samples.

Preferably the levels measured are concentrations of the analyte, and the sample of fluid which is mixed with the second known amount of analyte is of a known volume.

Providing more than one level of internal glucose calibration may allow even more accurate calibration of each result and thus even more accurate blood glucose testing. The need for batch calibration could also be correspondingly reduced.

In the methods of the present invention, the step of adjusting may also include making corrections based on one or more external factors such as ambient temperature or altitude. Thus the effect of environmental conditions on the measurements can be compensated for.

A second aspect of the present invention provides a device for measuring a level of a clinically relevant analyte in a fluid, including:

a flow path for conducting said fluid through the device;

a predetermined amount of said analyte arranged on said flow path such that the analyte mixes with fluid that passes it to form a calibration sample of the fluid;

detector means arranged on said flow path for detecting respective analyte levels in an unadulterated sample of the fluid and in the calibration sample.

Preferably the analyte is glucose.

In one embodiment, the predetermined amount of analyte is arranged as part of the detector means. For example, the analyte may be provided on a mesh which is used to spread the fluid at the detector means. In another example, the analyte is provided on a separate membrane which forms part of the detector means.

In a preferred arrangement, the detector means includes at least two detectors, a first of said detectors being arranged to detect the analyte level in the unadulterated sample, and a second of said detectors being arranged downstream of said predetermined amount of the analyte to detect the analyte level in the calibration sample.

In one embodiment of the above arrangement, said first and said second detectors are arranged in series on the flow path, and said predetermined amount of the analyte is located between said first and second detectors. Thus there may be a single flow path with the fluid passing, in order, the first detector, the predetermined amount of the analyte and the second detector. This embodiment has the advantage of only having a single flow path and so is relatively simple and cheap to manufacture.

In another embodiment of the above arrangement, the flow path divides into at least two branches, said first detector being arranged on a first of said branches and the predetermined amount of the analyte and said second detector being arranged on a second of said branches.

Thus there may be a parallel arrangement with one branch handling the unadulterated sample and another the calibration sample before and after mixing. This embodiment separates the two samples, thus avoiding the possibility of the measurement of one affecting the measurement of the other and also does not increase the overall measurement time relative to existing devices that do not incorporate this invention.

In an alternative parallel arrangement, there may be two separate flow paths with said first detector being arranged on a first of said flow paths and the predetermined amount of the analyte and said second detector being arranged on a second of said flow paths. The two flow paths may have separate openings to the exterior where the fluid is applied.

In an alternative preferred arrangement, the flow path divides into at least two branches of different lengths, said predetermined amount of analyte being located on one of said branches, and said branches rejoin upstream of the detector means, further wherein said branches are adapted so that fluid takes longer to flow through a first of said branches to the detector means than through a second of said branches.

The first and second branches may be of different lengths, or may have different flow rates.

The detector means may thus be a single detector which measures both the unadulterated sample and the calibration sample, with the difference in lengths of the branches of the flow paths causing the different samples to arrive at the detector at different times. A device with a single detector is cheaper to manufacture.

In this alternative arrangement the predetermined amount of glucose is preferably located on the first of the branches (e.g. the longer branch or the branch with the lower flow rate). This allows the unadulterated sample to be measured first, thus reducing possible complications due to mixing of the samples.

The detector means of this aspect may include at least one enzyme electrode.

The device of this aspect may further include a transducer or processor for processing signals from said detector means to produce an analyte level reading. The analyte level reading may be determined before or after an internal calibration process is applied, as described in relation to the first aspect above.

Preferably the transducer or processor is adapted to produce an analyte level reading by adjusting the analyte level detected in the unadulterated sample according to the analyte level detected in said calibration sample.

Preferably the flow path operates to draw the fluid through the device by capillary action. This may allow the amount of fluid flowing through the device to be known, enabling determination of the increased concentration of glucose in the calibration sample arising from mixing with a known amount of the analyte. This arrangement may also reduce the possibility of user error contributing to an error in the detected analyte levels.

In a development of the above aspect, the device further includes a second predetermined amount of the analyte arranged on said flow path such that it mixes with fluid that passes it to form a second calibration sample, and wherein said detector means is arranged on said flow path so as to detect an analyte level in the unadulterated sample, and in the calibration samples.

As with the method of the first aspect above, providing more than one level of internal analyte calibration may allow even more accurate calibration of each result and thus even more accurate analyte testing. The need for batch calibration could also be correspondingly reduced.

The two predetermined amounts of the analyte may be different amounts. This can provide more accurate calibration in devices in which the flow path branches. However, the predetermined amounts may be the same. Thus, in the case where the analyte level detectors are arranged in series on a flow path, the fluid passes, in order, a first detector, a first predetermined amount of the analyte, a second detector, a second predetermined amount of the analyte and a third detector.

The devices of the present invention may further include one or more sensors, which may be connected to the transducer or processor. The device, for example in the transducer or processor may process signals from the sensor(s) when producing an analyte level reading. The sensors may be, for example, temperature sensors.

The devices of the present invention are preferably portable, and so can be carried by the user and readily available for use in a wide variety of situations.

A further aspect of the present invention provides a method for testing, in a portable device, levels of a clinically relevant analyte in a fluid, including the steps of:

mixing a known amount of a calibration analyte into a sample of said fluid, the calibration analyte being a different species to said clinically relevant analyte;

measuring the level of said clinically relevant analyte in said sample;

measuring the level of said calibration analyte in said sample;

adjusting the measured level of said clinically relevant analyte using the measured level of said calibration analyte.

Preferably the clinically relevant analyte is glucose. Typically the fluid is blood.

Preferably the calibration analyte is a substance that is not naturally present in the fluid, and therefore its level in the sample is as a result of the known amount only. Alternatively the calibration analyte may be naturally present at a relatively low level, such that the level measured in the sample can be attributed to the added amount only and any error associated with ignoring the low natural level is insignificant. As a third option the calibration analyte may be naturally present at a relatively constant, known level and this level can then be subtracted from the total measured level in the sample.

Examples of calibration analytes that could be used in this context are substrates of the enzyme class of oxidoreductases acting on the CH—OH group of donors with oxygen as an acceptor (i.e. the group EC 1.1.3), such as cellobiose and xylitol. Alternatively substrates of synthetic enzymes (e.g. catalytic antibodies) could be used as the calibration analyte.

In the method of the present aspect the response of the measurement system used to the calibration analyte can be taken to be the same as the response of the measurement system to the clinically relevant analyte, and in particular may be subject to the same interferences. Thus the measured level of the clinically relevant analyte can be adjusted according to a factor derived from any difference between the measured level of the calibration analyte and the known amount (or concentration) added to the sample.

Preferably the steps of measuring involve measuring a concentration of the respective analyte. This may also include mixing a known volume of fluid with the known amount of said calibration analyte in said mixing step.

As with the previous aspects of the invention, providing internal calibration of every sample tested, at the point of use, allows potential variations in the test result arising from sample effects, environmental factors and manufacturing imprecision to be accounted for and the test results adjusted accordingly. Therefore errors in the test results can be substantially reduced, or even effectively eliminated.

Similarly to the previous aspects, if the method of the present invention is used to its fullest extent, then the amount of batch calibration carried out can be reduced.

A further aspect of the present invention provides a device for measuring a level of a clinically relevant analyte in a fluid, the device including:
  a flow path for conducting said fluid through the device;
  a predetermined amount of a calibration analyte arranged on said flow path such that the calibration analyte mixes with fluid that passes it to form a calibration sample, the calibration analyte being a different species to said clinically relevant analyte;
  first detector means arranged on said flow path for detecting a level of said clinically relevant analyte in the calibration sample; and
  second detector means arranged on said flow path for detecting a level of said calibration analyte in the calibration sample.

Preferably the clinically relevant analyte is glucose.

Preferably the calibration analyte is a substance that is not naturally present in the fluid, and therefore its level in the sample is as a result of the known amount only. Alternatively the calibration analyte may be naturally present at a relatively low level, such that the level measured in the sample can be attributed to the added amount only and any error associated with ignoring the low natural level is insignificant. As a third option the calibration analyte may be naturally present at a relatively constant, known level and this level can then be subtracted from the total measured level in the sample.

Examples of calibration analytes that could be used in this context are substrates of the enzyme class of oxidoreductases acting on the CH—OH group of donors with oxygen as an acceptor (i.e. the group EC 1.1.3), such as cellobiose and xylitol. Alternatively substrates of synthetic enzymes (e.g. catalytic antibodies) could be used as the calibration analyte. The first and/or second detector means of this aspect may include at least one enzyme electrode.

The first and second detector means may be arranged at the same location on the flow path. This co-location may be preferred where the calibration analyte (or the electrochemical species produced as consequence of reaction with that analyte) and the clinically relevant analyte (or the electrochemical species produced as a consequence of reaction with that analyte) can be specifically and independently measured.

Alternatively the first and second detector means may be arranged separately on the flow path. In this instance, the electrochemical species generated from both analytes may be the same (e.g. hydrogen peroxide). An advantage of this arrangement is that a biological receptor part of the sensor (e.g. an enzyme) can be similar or identical for both the first and second detector means (i.e. the clinically relevant analyte and the calibration analyte are subject to similar or identical measurement processes) and would therefore be liable to similar interferences.

Preferably the flow path operates to draw the fluid through the device by capillary action. This may allow the amount of fluid flowing through the device to be known, thus facilitating calculation of concentrations. This arrangement may also reduce the possibility of user error contributing to an error in the detected analyte levels.

Preferably the first and second detector means are arranged on a single capillary channel. Thus only a single flow path need be provided on the device, and the device can be relatively simple and cheap to manufacture.

The device of this aspect may further include a transducer or processor for processing signals from the detector means to produce an analyte level reading. The analyte level reading may be determined before or after an internal calibration process is applied as described in relation to the previous aspect.

Preferably the transducer or processor is adapted to produce an analyte level reading by adjusting the analyte level of the clinically relevant analyte detected according to the analyte level of the calibration analyte detected.

The device of the present aspect may further include one or more sensors, which may be connected to the transducer or processor. The device, for example in the transducer or processor, may process signals from the sensor(s) when producing an analyte level reading. The sensors may be, for example, temperature sensors.

Figure 2:
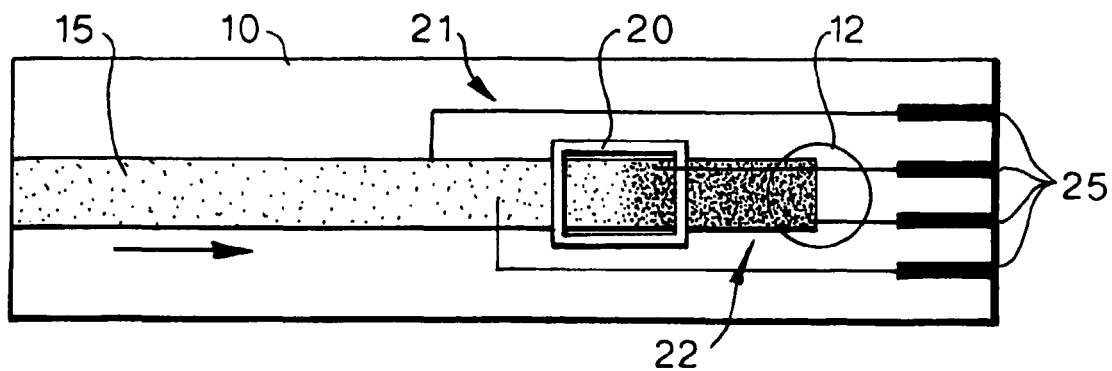

Embodiments of the present invention will now be described with reference to the accompanying drawings, in which:

FIG. 1 is a schematic illustration of part of a blood glucose monitoring device according to a first embodiment of the present invention; and FIG. 2 is a schematic illustration of part of a blood glucose monitoring device according to a second or a third embodiment of the present invention.

In an embodiment of a method of the present invention, the internal calibration is achieved by incorporating a well-defined known amount of glucose into the test sample and measuring the blood glucose response in both the presence and in the absence of the added glucose. The difference between the signal generated by the two samples is used to modify the unadulterated sample result.

An example situation is given below, in which the numbers have been chosen for purely illustrative purposes:

|  | Normal Hct | High Hct | Low Hct |
|---|---|---|---|
| Unadulterated test result (mM) | 5 | 4 | 6 |
| Calibration result (mM) | 10 | 8 | 12 |
| Adjusted result (mM) | 5 | 5 | 5 |

The adjusted concentration result is obtained as:

Unadulterated Result×known increase in glucose concentration in calibration sample (calibration result−unadulterated result)

This illustrative table demonstrates how a source of error can be eliminated from blood glucose measurements by using the internal calibration approach. In the example given, the unadulterated test result varies as a consequence of different Hct levels in the test blood, despite the fact that the glucose concentration is 5 mM in all cases. However the effect of the Hct level can be determined by observing the difference in measured concentrations between the unadulterated sample and the calibration sample, to which a known increase in concentration has been effected. Once the extent of the interference arising from Hct has been gauged, it is a relatively straightforward matter to correct for this effect. This illustration uses Hct as an example interferent, but the same rationale applies to other interferences or sources of error.

Other, more complex, algorithms could be used to modify the test result. For example different weightings could be given to the internal calibration and batch calibration in the calculation of glucose concentrations, for example:

Calculated glucose concentration=(glucose concentration derived from batch calibration+adjusted glucose concentration derived from internal calibration)/2.

Embodiments of the devices of the present invention are illustrated in FIGS. 1 and 2. Each embodiment has a sensor strip 10 which has a capillary fill mechanism and a capillary flow path 15 that allows a portion of the test sample to mix with a known amount of glucose. The portion of the sample that is mixed with the known amount of glucose is measured at a second separate detector 22, which in both embodiments is an enzyme electrode, on the same sensor strip as the first detector 21 measuring the unadulterated test sample, which is also an enzyme electrode in both embodiments. The flow directions in FIGS. 1 and 2 are shown by the arrows.

The first embodiment, shown in FIG. 1, has a "parallel" configuration with the capillary flow path 15 dividing into branches 16 and 17. One branch 16 passes directly to a first test well 18 where the glucose is measured by the first enzyme electrode 21. The other branch 17 passes over and mixes with an accurately known amount of dried glucose 20 to a second test well 19 where the glucose is measured by the second enzyme electrode 22. Air vents 12 are provided to allow capillary flow and to provide sufficient oxygen at the enzyme electrodes 21 and 22 for the electrode reaction to occur.

The second embodiment, shown in FIG. 2, has a "serial" configuration with an undivided capillary flow path 15. The flow path 15 conducts the test sample past a first enzyme electrode 21 which measures the glucose content of the unadulterated test sample. The flow path 15 then conducts the test sample to mix with an accurately known amount of dried glucose 20 to a second enzyme electrode 22 which measures the glucose concentration of the calibrated sample.

Connectors 25 are provided in both embodiments for connection of the device to a transducer (not shown) which converts the signals from the electrodes into readable results and applies the appropriate algorithm(s) to calibrate the results.

A further embodiment of a device of the present invention has a second capillary track in the course of which the test sample is mixed with a known amount of glucose. This second capillary track follows a convoluted or impeded path from the site of the blood application to a detector such as an enzyme electrode. The unadulterated blood sample follows a much more direct path to the same enzyme electrode. Thus the internally calibrated blood sample will arrive at the electrode later than unadulterated sample. This time difference allows the glucose concentration or content of the unadulterated blood sample to be measured before mixing with the internally calibrated sample. Once the two samples mix, a second reading can be taken where the added glucose concentration is known, thus providing the internal calibration reading.

In the above embodiments, the known amount of glucose is arranged on the flow path so that the calibration sample passes and mixes with it prior to arriving at the detector electrode. However, it is also possible that the known amount of glucose may be formed as part of the detector electrode for the calibration sample itself.

A standard form of an enzyme electrode is made up of a number of layers. The first is a conductive track, on top of which is the layer containing the enzyme (e.g. glucose oxidase) and, potentially, redox mediators. Above this is a mesh which serves to spread out the blood or other fluid being tested. A membrane can be provided between the mesh and the electrode surface to physically, chemically or electronically prevent interferents from reaching the enzyme electrode.

The known amount of glucose could be provided on the mesh layer, as an additional membrane layer, or in place of any membrane layer. The glucose membrane layer may comprise a known amount of glucose distributed over a mesh, or may be made of a film containing a known amount of glucose that is expended in the measurement process.

In both the above embodiments, it is preferable that the amount of glucose used for the calibration sample is accurately and precisely known. In order to achieve this, any one of a number of techniques may be used to apply the glucose to the device. Examples of such techniques are printing technologies (e.g. ink-jet, screen, gravure or flexographic printing), dispensing technologies (e.g. syringe driven), metering of glucose-loaded beads, deposition of glucose onto a solid-phase substrate such as paper or string.

It is also preferable that the calibration glucose on the sensor strip mixes quickly and homogeneously with the blood sample which passes it. This can be achieved through the placement pattern of the dried glucose on the strip or the formulation of the dried glucose or a combination of the above. The placement pattern may utilise the capillary floor, walls and lid. Adjusting the formulation of the glucose can increase the rate of dissolution. Particular techniques which may be applied are micronisation of the glucose powder, co-formulation into rapidly re-suspending hydrocolloids forming a membrane, co-formulation with ingredients generating effervescence when re-suspended or freeze-drying to form a high porosity stable crystalline structure.

A device according to a third embodiment of the invention has many features in common with the device of the second embodiment described above, and reference will be made to the appropriate parts of FIG. 2 in describing this embodiment.

The device according to this embodiment has a "serial" configuration with an undivided capillary flow path 15. In this embodiment, the flow path 15 first conducts the test sample to a first enzyme electrode 21 which measures the glucose content of the test sample. The flow path 15 then conducts the test sample to mix with an accurately known amount of a calibration analyte 20, which in the present embodiment is cellobiose. The flow path 15 then conducts the test sample to a second enzyme electrode 22 which measures the concentration of the calibration analyte in the test sample.

In this embodiment the glucose concentration measured is adjusted by a factor generated from the difference between the measured and actual, known concentration of calibration analyte. For example, if the added amount of calibration analyte was known to produce a concentration of 30 mM in the volume of blood in which it dissolves, but the concentration measured was 20 mM, then a factor of 1.5 (30 mM/20 mM) would be used to adjust the measured glucose concentration upwards. In this embodiment of the invention, the validity of this factor in adjusting blood glucose concentrations based on measurement of a different analyte would be based on the two systems having similar interference profiles.

Optional or preferred features of the first and second embodiments above, such as the manner or mechanism by which the calibration glucose is positioned or placed on the sensor strip, are equally applicable to this embodiment.

The precise details of the construction and manufacture of sensor strips is well known in the art, and the present invention can be embodied in sensor strips which are made from a wide variety of materials and by a wide variety of methods.

One example of a sensor strip is described here, purely for illustrative purposes. The strip has overall dimensions of 30×10×2 mm. The substrate and cover defining the capillary flow path are comprised of a flexible plastic, and the capillary cover is adhered to the base substrate by means of a pressure sensitive adhesive. Electrode tracks are formed from conductive screen printing inks and active electrodes are manufactured by screen printing an enzyme solution (potentially including a redox mediator) onto an underlying conductive track. The reference electrode has no enzyme overlaid. Generally such products are single use disposable products.

The readings from the detector may be used to provide a blood glucose level reading and/or a calibration analyte reading as previously described. The internal calibration using the measurement from the calibration sample or analyte may be applied directly to the unprocessed measurements from the detector measuring the glucose level (in the unadulterated sample in the first and second embodiments), or applied to a blood glucose level reading which has been derived from the unprocessed measurements.

For example, the sensor strip of an embodiment of the present invention may be connected to a transducer which produces blood glucose level readings from an electrical input from an enzyme electrode detector by applying a calibration curve. The reading obtained may then be adjusted and corrected depending on the measurement from the calibration sample.

Alternatively, the electrical signal from the enzyme electrode detector may be adjusted or corrected as a result of the measurement from the calibration sample or analyte to create a corrected electrical signal which is then used by a transducer or processor to produce a corrected blood glucose level reading, for example by applying a calibration curve.

Although the above description has been made with specific references to the testing of glucose in blood, it will be clear to the person skilled in the art that the principles could be applied to other clinically relevant analytes such as indicators of cardiovascular, liver and kidney function (e.g. cholesterol, haemoglobin, electrolytes, metabolites), infectious agents (e.g. viruses, bacteria), disease state indicators (e.g. C-reactive protein, antibodies, cellular signalling factors, hormones) and therapeutic indicators (e.g. antibiotics and drugs), which may be contained in other samples of biological origin such as cerebrospinal fluid, urine, semen and saliva.

The invention claimed is:

1. A device for measuring a level of a clinically relevant analyte in a fluid, including:
a flow path for conducting said fluid through the device;
a predetermined amount of said analyte arranged on said flow path such that the analyte mixes with fluid that passes it to form a calibration sample of the fluid;
detector means arranged on said flow path for detecting respective analyte levels in an unadulterated sample of the fluid and in the calibration sample.

2. A device according to claim 1 wherein said predetermined amount of analyte is arranged as part of the detector means.

3. A device according to claim 1 wherein said detector means includes at least two detectors, a first of said detectors being arranged to detect the analyte level in the unadulterated sample, and a second of said detectors being arranged downstream of said predetermined amount of analyte to detect the analyte level in the calibration sample.

4. A device according to claim 3 wherein said first and said second detectors are arranged in series on the flow path, and said predetermined amount of analyte is located between said first and second detectors.

5. A device according to claim 3 wherein said flow path divides into at least two branches, said first detector being arranged on a first of said branches and the predetermined amount of analyte and said second detector being arranged on a second of said branches.

6. A device according to claim 3 wherein there are two separate flow paths, said first detector being arranged on a first of said flow paths and the predetermined amount of analyte and said second detector being arranged on a second of said flow paths.

7. A device according to claim 1 wherein said flow path divides into at least two branches, said predetermined amount of analyte being located on one of said branches, and said branches rejoin upstream of the detector means and further wherein said branches are adapted so that fluid takes longer to flow through a first of said branches to the detector means than through a second of said branches.

8. A device according to claim 7 wherein the first and second branches are of different lengths.

9. A device according to claim 7 wherein the first and second branches have different flow rates.

10. A device according to claim 7 wherein said predetermined amount of analyte is located said first branch.

11. A device according to claim 7 wherein said detector means is a single detector.

12. A device according to claim 1 including a processor which is adapted to produce an analyte level reading by adjusting the analyte level detected in the unadulterated sample according to the analyte level detected in said calibration sample.

13. A device according to claim 1 further including a second predetermined amount of said analyte arranged on said flow path such that it mixes with fluid that passes it to form a second calibration sample, and wherein said detector means is arranged on said flow path so as to detect an analyte level in an unadulterated sample, and in the calibration samples.

14. A device according to claim 13 wherein the predetermined amounts of said analyte are different amounts.

15. A device according to claim 1 wherein said clinically relevant analyte is glucose.

16. A device according to claim 1 wherein said detector means includes at least one enzyme electrode.

17. A device according to claim 1 further including a processor for processing signals from said detector means to produce an analyte level reading.

18. A device according to claim 17 further including a sensor connected to said processor, wherein the processor also processes signals from said sensor to produce an analyte level reading.

19. A device according to claim 1 wherein said flow path operates to draw the fluid through the device by capillary action.

20. A device for measuring a level of a clinically relevant analyte in a fluid, the device including:
a flow path for conducting said fluid through the device;
a predetermined amount of a calibration analyte arranged on said flow path such that the calibration analyte mixes with fluid that passes it to form a calibration sample, the calibration analyte being a different species to said clinically relevant analyte;
first detector means arranged on said flow path for detecting level of said clinically relevant analyte In the calibration sample; and
second detector means arranged on said flow path for detecting a level of said calibration analyte in the calibration sample, wherein the first and second detector means are arranged on a single channel of the flow path.

21. A device according to claim 20 wherein the first and second detector means are arranged at the same location on the flow path.

22. A method for testing, in a portable device, levels of clinically relevant analytes in a fluid including the steps of:
mixing a sample of the fluid with a known amount of said analyte to form a calibration sample;
measuring the analyte level in an unadulterated sample of the fluid;
measuring the analyte level in said calibration sample; and
adjusting the analyte level measured in said unadulterated sample using the analyte level measured in said calibration sample.

23. A method according to claim 22 further including the step of generating an analyte level reading from said adjusted analyte level, wherein said step of adjusting is carried out on the unprocessed measurement of the analyte level in the unadulterated sample.

24. A method according to claim 23 wherein the analyte level reading is generated by applying a calibration curve to the analyte level.

25. A method according to claim 22 further including the step of generating an analyte level reading from the measurement of the analyte level in the unadulterated sample, wherein said step of adjusting is carried out on the analyte level reading.

26. A method according to claim 22 wherein in the adjusting step, the expression used to calculate an adjusted analyte concentration is:

$$Gl_{adj} = (Gl_{un} \times Q)/(Gl_{cal} - Gl_{un})$$

where $Gl_{adj}$, $Gl_{un}$ and $Gl_{cal}$ are respectively the adjusted analyte concentration, the analyte concentration measured in the unadulterated sample of the fluid, and the analyte concentration measured in the calibration sample and Q is the known increase in concentration of analyte in the calibration sample resulting from the addition of a known amount of analyte to a known volume of sample.

27. A method according to claim 22 further including the steps of mixing a sample of the fluid with a second known amount of analyte to form a second calibration sample, and measuring the analyte level in said second calibration sample, wherein the step of adjusting uses the analyte levels measured in both calibration samples.

28. A method according to claim 27 wherein the sample of fluid which is mixed with the second known amount of analyte is of a known volume.

29. A method according to claim 22 wherein the clinically relevant analyte is glucose.

30. A method according to claim 22 wherein the fluid is blood.

31. A method according to claim 22 wherein said steps of measuring involve measuring a concentration of analyte.

32. A method according to claim 22 wherein in said step of mixing, a known volume of fluid is mixed with the known amount of said analyte.

33. A method according to claim 22 further including the step of introducing said fluid to a flow path, and wherein said fluid flows along the flow path whilst said steps of measuring and mixing are carried out.

34. A method according to claim 22 wherein said step of adjusting includes making corrections based on one or more external factors.

35. A method according to claim 34 wherein at least one of said external factors is the ambient temperature.

* * * * *